United States Patent
Prescott

(10) Patent No.: US 10,433,856 B2
(45) Date of Patent: Oct. 8, 2019

(54) SURGICAL DRILL HANDPIECE WITH ADJUSTABLE CUTTING TOOL GUARD

(71) Applicant: Grace Medical, Inc., Memphis, TN (US)

(72) Inventor: Anthony D. Prescott, Arlington, TN (US)

(73) Assignee: Grace Medical, Inc., Memphis, TN (US)

( * ) Notice: Subject to any disclaimer, the term of this patent is extended or adjusted under 35 U.S.C. 154(b) by 559 days.

(21) Appl. No.: 15/207,181

(22) Filed: Jul. 11, 2016

(65) Prior Publication Data
US 2018/0008288 A1    Jan. 11, 2018

(51) Int. Cl.
  *A61B 17/16*      (2006.01)
  *A61B 17/00*      (2006.01)
  *A61B 90/00*      (2016.01)

(52) U.S. Cl.
  CPC ........ *A61B 17/1622* (2013.01); *A61B 17/162* (2013.01); *A61B 17/1615* (2013.01); *A61B 17/1633* (2013.01); *A61B 17/1624* (2013.01); *A61B 17/1628* (2013.01); *A61B 17/1631* (2013.01); *A61B 2017/0042* (2013.01); *A61B 2090/036* (2016.02); *A61B 2090/08021* (2016.02)

(58) Field of Classification Search
  CPC .............. A61B 17/1615; A61B 17/162; A61B 17/1622; A61B 17/1624; A61B 17/1628; A61B 17/1631; A61B 17/1633; A61B 17/17; A61B 2017/0042; A61B 2090/08021; A61B 2090/036
  See application file for complete search history.

(56) References Cited

U.S. PATENT DOCUMENTS 3,712,352 A    1/1973 Lafferty, Sr.
4,232,535 A   11/1980 Caldwell
(Continued)

FOREIGN PATENT DOCUMENTS

EP    1732452    7/2010

OTHER PUBLICATIONS

Otologic Drills and Burs, Revolutionary Design for Neurotology, Medtronic Inc., 2008.
(Continued)

*Primary Examiner* — Kevin T Truong
*Assistant Examiner* — Tracy L Kamikawa
(74) *Attorney, Agent, or Firm* — Gordon & Jacobson, P.C.

(57) ABSTRACT

A system includes a handpiece and a removable tool assembly including a holder body, a shaft, a medical tool, a guard, and a sleeve. The body engages the handpiece and defines a bore. The shaft extends within the bore and the tool is provided to the distal end of the shaft. The guard is coupled to the body via a snap fit connection at the bore and may be friction fit to a bearing sleeve located between the guard and the shaft, such that longitudinal translation of the guard relative to the body longitudinally displaces the guard. The shaft extends within the bore of the body and the guard. The guard is positioned relative to the body by a distance to define a working length of the tool between the distal end of the guard and the distal tip of the tool. The working length of the tool may be used to cut tissue, without concern that cutting will be deeper than intended.

30 Claims, 10 Drawing Sheets

(56) References Cited

U.S. PATENT DOCUMENTS

| | | | |
|---|---|---|---|
| 4,486,176 A | 12/1984 | Tardieu et al. | |
| 4,568,642 A | 2/1986 | DeForrest et al. | |
| 4,705,038 A | 11/1987 | Sjostrom et al. | |
| 4,811,736 A | 3/1989 | Griggs et al. | |
| 4,964,839 A | 10/1990 | Gloor | |
| 4,995,877 A | 2/1991 | Ams et al. | |
| 5,217,479 A * | 6/1993 | Shuler | A61B 17/32002 600/564 |
| 5,263,218 A | 11/1993 | Giuliani et al. | |
| 5,405,348 A | 4/1995 | Anspach, Jr. et al. | |
| 5,569,967 A | 10/1996 | Rode | |
| 5,609,602 A | 3/1997 | Machemer et al. | |
| 5,796,188 A | 8/1998 | Bays | |
| 5,810,828 A | 9/1998 | Lightman et al. | |
| 6,047,456 A | 4/2000 | Yao et al. | |
| 6,126,670 A | 10/2000 | Walker et al. | |
| 6,425,761 B1 | 7/2002 | Eibofner | |
| 6,517,560 B1 | 2/2003 | Toth et al. | |
| 6,722,668 B2 | 4/2004 | Huggins et al. | |
| 6,887,244 B1 | 5/2005 | Walker et al. | |
| 7,210,881 B2 | 5/2007 | Greenberg | |
| 7,294,947 B2 | 11/2007 | Corbin, III et al. | |
| 7,337,697 B2 | 3/2008 | Bader et al. | |
| 7,442,197 B2 * | 10/2008 | Abdelgany | A61B 17/17 606/96 |
| 7,618,428 B2 * | 11/2009 | O'Quinn | A61B 17/32002 606/159 |
| 7,771,143 B2 * | 8/2010 | Bharadwaj | A61B 17/1633 408/1 R |
| 8,126,564 B2 | 2/2012 | Gantz | |
| 8,403,916 B2 * | 3/2013 | Prescott | A61B 17/32002 335/306 |
| 8,523,873 B2 * | 9/2013 | Bharadwaj | A61B 17/1633 600/554 |
| 9,155,545 B2 | 10/2015 | Prescott | |
| 2003/0040763 A1 | 2/2003 | Moutafis et al. | |
| 2006/0264955 A1 | 11/2006 | Abdelgany | |
| 2008/0234664 A1 | 9/2008 | May et al. | |
| 2010/0094306 A1 | 4/2010 | Chang et al. | |
| 2011/0125176 A1 | 5/2011 | Yates et al. | |
| 2013/0072935 A1 * | 3/2013 | Matsuda | A61B 17/32002 606/79 |
| 2014/0324050 A1 | 10/2014 | Masson | |
| 2015/0119889 A1 * | 4/2015 | Prescott | A61B 17/1679 606/80 |
| 2017/0189036 A1 | 7/2017 | Rajeev | |

OTHER PUBLICATIONS

"K161376" (Department of Health & Human Services), Aug. 25, 2016, retrieved from the internet Aug. 23, 2017; <URL=https://www.accessdata.fda.gov/cdrh_docs/pdf16/K161376.pdf>.

* cited by examiner

SURGICAL DRILL HANDPIECE WITH ADJUSTABLE CUTTING TOOL GUARD

CROSS-REFERENCE TO RELATED PATENTS

This application is related to U.S. Pat. Nos. 8,403,916 and 9,155,545, which are hereby incorporated by reference herein in their entireties.

BACKGROUND

1. Field

The present disclosure relates to surgical instrumentation, and more particularly surgical drill handpieces. More specifically, the invention relates to handpieces for driving otology burs and guards therefor which are advantageously used during a cochleostomy and other surgical procedures in which it is desired to protect one anatomic structure by controlling the depth of a cutting instrument while removing another structure with the cutting instrument.

2. State of the Art

A cochlear implant is a hearing device that can be implanted in an individual with a severe or profound sensorineural hearing loss to directly stimulate the cochlear nerves and restore hearing. When successfully implanted, the cochlear implant restores a sufficient sense of sound, albeit with a different quality than natural sound, so that the recipient is able to hear and understand speech and environmental sounds. The performance of the cochlear implant is greater when there is some residual acoustic hearing capacity and a hearing aid is used in conjunction with the cochlear implant. See, for example, U.S. Pat. No. 8,126,564 to Gantz. In order to preserve the acoustic hearing, it is of vital importance that the membranous structures of the cochlea not be damaged during the surgical implant procedure.

The implant includes an external portion and an internal portion. The external portion is surgically placed under the skin behind the ear, and includes one or more microphones which picks up sound from the environment, a speech processor which selectively filters sound to prioritize audible speech, splits the sound into channels and sends the electrical sound signals through a thin cable to the transmitter, and a transmitter, which is a coil held in position by a magnet placed behind the external ear, and transmits power and the processed sound signals across the skin to the internal device by electromagnetic induction. The internal portion is secured in the cochlear bone beneath the skin, and includes a receiver and stimulator, which converts the signals into electric impulses and sends them through an internal cable to electrodes. The electrodes are wound through the cochlea, send the impulses to the nerves in the scala tympani and then directly to the brain through the auditory nerve system.

In order to pass the electrodes, a small hole must be drilled into the bony cochlea. A high-speed bur driving surgical handpiece is used to drill into the cochlea. However, it is a very delicate procedure, and extreme precision is required to ensure that the hole is drilled through the boney outer surface of the cochlea, but that no damage results to the interior cochlear membranes. The difficultly is rendered higher given that the depth of the boney surface is not consistent among patients. The surgeon must progressively remove bone from the cochlear wall while visually observing the color change at the bony surface to determine when the cochlear wall is about to be penetrated with the bur.

In such procedures, it is known to use a bur guard about the rotating shaft of the bur to protect peripherally surrounding tissue from the rapidly rotating shaft of the bur. However, such burs do not practically operate to limit the drilling depth of the bur.

SUMMARY

A medical tool system according to the invention includes a surgical tool handpiece (e.g., ahigh-speed otologic driver handpiece), a tool mount, and a medical tool assembly driven by the handpiece. The tool assembly may include a tool holder body, a tool shaft, a medical tool (e.g., a bur, cutting tool or the like), a tool guard, and bearing sleeve between the tool shaft and the tool guard. The tool holder body has a proximal portion that engages a socket of the tool mount provided to the handpiece, a distal end, and defines a longitudinal bore extending through the body. The tool shaft extends within the bore and is permanently retained relative to the tool holder body. The tool shaft has proximal structure by which the driver handpiece is adapted to drive the tool shaft about a tool shaft axis. The tool (e.g., cutting bur) is fixed or replaceable relative to the distal end of the tool shaft, with movement (e.g., rotation) of the tool shaft resulting in corresponding movement (e.g., rotation) of the tool (e.g., cutting bur) in a cutting motion. The tubular tool guard has a proximal end coupled to the tool holder body, preferably via a radial engagement arrangement at the bore of the tool holder body. The tubular guard may be configured for fixed or relative longitudinal movement with the tool holder body. The bearing sleeve is retained in the bore of the holder body and extends within the bur guard, and provides for stable and free movement (e.g., rotational and/or longitudinal) of the tool shaft.

The guard has an inner diameter and open distal end sized to permit advancement of the tool therethrough. Displacement of the distal end of the guard relative to the holder body sets a defined working (e.g., cutting) length of the tool extending beyond the distal end of the guard. The distal end of the guard functions as a stop to prevent working (e.g., cutting) deeper than the set working length of the tool, even though the tool may have a significantly longer length extending within and protected by the guard.

In accord with preferred aspects of the invention, the guard includes a plurality of tabs and associated slots extending longitudinally a proximal end of the guard. The tool holder body has an elongated slot that radially engages or otherwise interfaces with the tabs of the guard to set a relative cutting depth between the distal end of the guard and the distal end of the tool. The tabs on the guard may be set to allow fixed positioning of the guard relative to the tool holder body and the tool or to allow displaceable positioning. The tool holder body and the guard may be provided with respective indicia to indicate the amount of relative movement therebetween, and, thus, the working length of the tool.

In use, the guard may be moved or otherwise set relative to the tool holder body so that the distal end of the guard is even with the distal tip of the tool. Then, the guard may be retracted relative to the tool holder body by a set distance to define an exposed length of the tool between the distal end of the guard and the distal tip of the tool. The exposed length of the tool is then used to operate on tissue, without concern that such work will be deeper than intended. Particularly, the hard tissues of the ear, including the cochlea can be cut with a cutting tool while protecting the delicate interior membranes.

DETAILED DESCRIPTION

Figure 1:
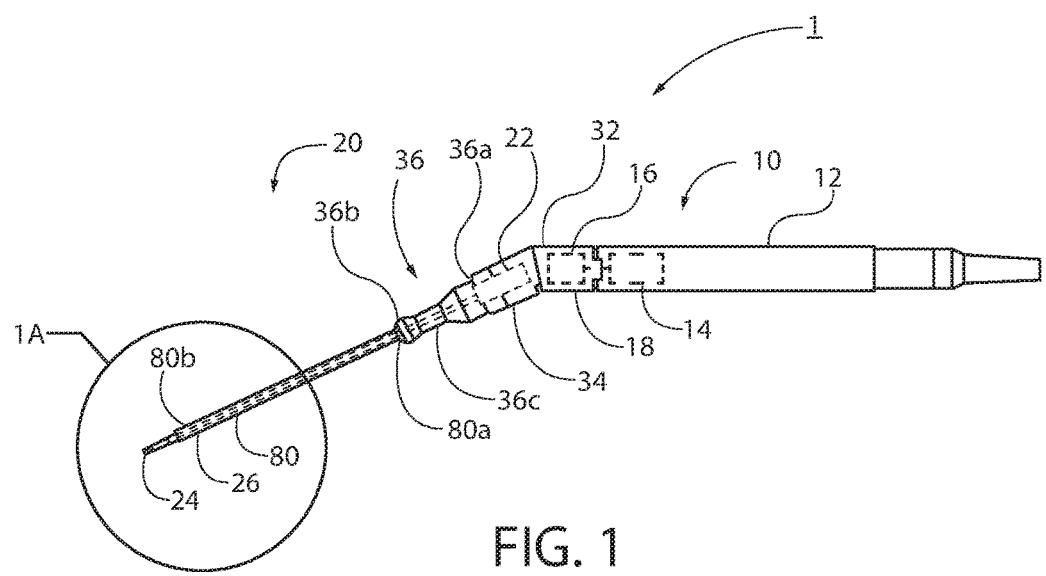
FIG. 1 shows an embodiment of a medical tool system in accordance with an aspect of the invention.

Referring to FIG. 1, a system 1 according to an embodiment of the invention is shown. The system generally includes a handpiece 10 (e.g., an otology drill handpiece), a tool mount 18, and a replaceable tool assembly 20 retained relative to the handpiece.

The handpiece 10 includes a housing 12, an electric motor 14 mounted within the housing, a drive magnet 16 housed within the housing 12 and coupled to and rotated by the motor 14, and a tool mount 18 preferably detachably coupled to the housing 12, but optionally fixed relative thereto. The handpiece 10 may be the same as handpiece 10 described in U.S. Pat. No. 9,155,545, the entire contents of which are incorporated by reference. The replaceable tool assembly 20 is detachably coupled to the handpiece 10 at the tool mount 18. Also, the tool mount 18 may be the same as tool mount 18 described in U.S. Pat. No. 9,155,545.

Figure 1A:
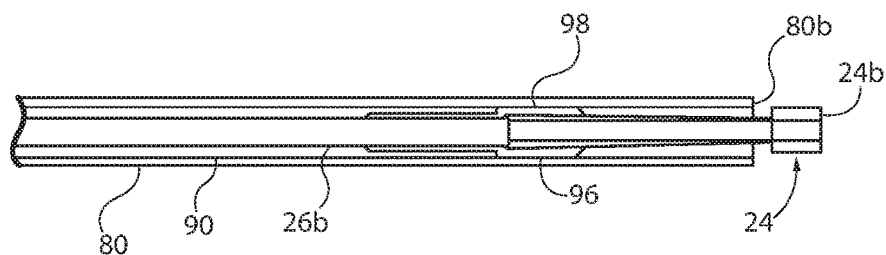
FIG. 1A is a longitudinal section view of portion 1A of the system shown in FIG. 1.

Referring to FIGS. 1 and 1A, the replaceable tool assembly 20 includes a tool holder body 36, a tool shaft 26 (which extends substantially the entire length of the cutting tool assembly 20, a medical tool 24 (described hereinfor example in the form of a cutting bur bit), a tubular tool guard 80 (described herein for example in the form of a bur guard), and a bearing sleeve 90 (FIG. 1A) radially disposed between the tool guard 80 and the tool shaft 26. The construction of the tool shaft 26, tool 24, and bearing sleeve 90 may be the same as the corresponding elements described in U.S. Pat. No. 9,155,545. The connection between the tool holder body 36 and a socket 34 of the tool mount 18 is preferably via an interference fit accommodated by a tapered fit of a proximal portion 36a of the tool holder body 36 within the socket 34 of the mount 18, or via another mechanical engagement. The tool mount 18 positions and retains the tool housing 36 of the tool assembly 20 such that the tool magnet 22 of the cutting tool 20, which is directly connected to the tool shaft 26, is in magnetic communication (i.e., magnetic coupling) with the drive magnet 16 (driven by the motor 14) of the handpiece 10. In this manner, rotation of the drive magnet 16 by the handpiece 10 causes movement (e.g., rotation) of the tool magnet 22, and consequent movement of the tool shaft 26 (within the bearing sleeve 90) and tool 24. Details of this arrangement are also described in U.S. Pat. No. 9,155,545. A magnetic drive arrangement with drive magnet is also described in more detail in U.S. Pat. No. 8,403,916, the entire contents of which are incorporated by reference. For purposes of a surgical procedure of interest, i.e., performing a cochleostomy, the tool 24 is preferably a cutting bur 24 having a diameter of less than 1.4 mm. Tools of other sizes could certainly be used, sized to the appropriate procedure.

It will be appreciated that various replaceable mounts and tool assemblies may be used in conjunction with the tool assembly 20 during one or more medical procedures to change the angle of the tool assembly 20 relative to the drive axis as well as the tool which is utilized with the system 1. The structure of the mount 18 and the tool assembly 20, in conjunction with forces applied to the tool magnet 22 via a magnetic coupling between the drive magnet 16 and the tool magnet 22 guide the movement of the tool 24 in rotation, oscillation, and/or longitudinal translation on or about the shaft axis. The medical tool 24 is fixed to a distal end 26b of the shaft 26, and thus rotates (360 degrees or oscillates) and/or longitudinally translates with the shaft 26. The tool 24 may be a cutter, a drill, a file, or any number of other similar devices as discussed below.

Figure 1B:
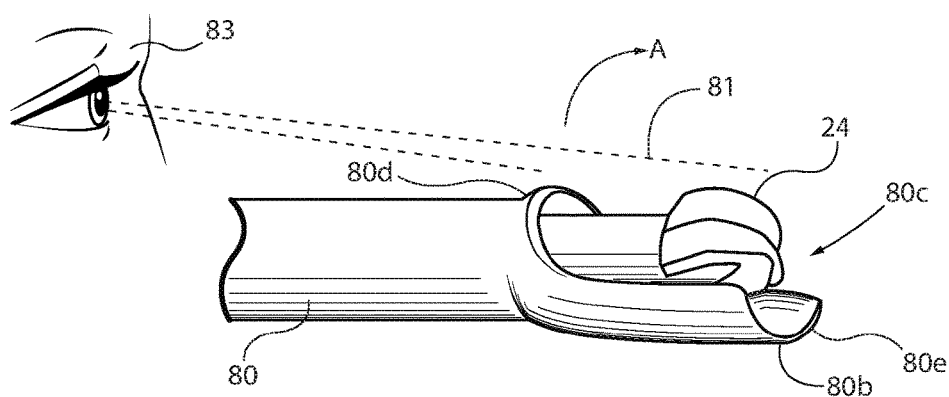
FIG. 1B is a view of a notched end of a tool guard shrouding a cutting tool, as shown in FIG. 1.
Figure 1C:
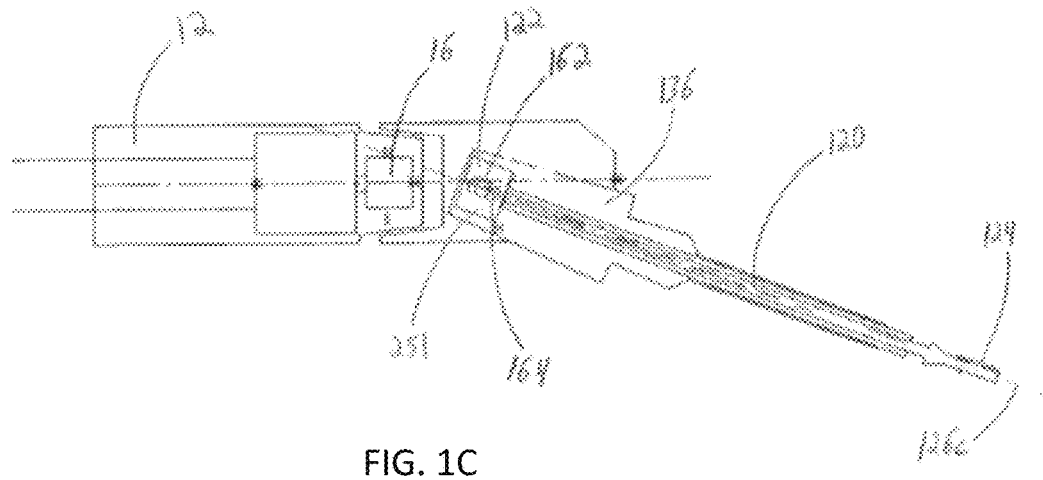
FIG. 1C is a schematic view of the medical tool system incorporating a second tool assembly included in a kit.

As discussed above, the system 1 may utilize one or more mounts and one or more tool assemblies for a given medical procedure or for different medical procedures. The exemplary embodiment of the tool assembly 20 shown in FIG. 1A allows for rotation of the tool 24, but not longitudinal translation. Turning to FIG. 1C, the system 1 is shown with a tool assembly 120 which allows for longitudinal translation of a tool 124. The tool assembly 120 includes at least one attachment pin 162 extending from and fixed to at least one side of a tool magnet 122. A tool holder 136 defines at least one slot 164 for slidably receiving the at least one attachment pin 162. The slot 164 extends in a generally parallel direction relative to a shaft axis 126 c. Thus, the slot 164 prevents rotation of the tool magnet 122 and the tool 124 about the shaft axis 126 c (the pin 162 can only move along the slot 164 in the direction of the shaft axis 126 c) while allowing for limited translation of the tool magnet 122 and tool 124 relative to the housing 12 or tool holder 136.

Rotation of the drive magnet 16 applies a force on the tool magnet 122 on account of the magnetic coupling therebetween. As the slot 164 limits movement of the tool 124 to longitudinal translation, the force will translate the tool 124 distally when the poles of the magnets 16, 122 repel each other and proximally when the poles attract each other. Thus, one complete 360° rotation of the drive magnet 16 will cause the tool 124 to move through the translational range allowed by the slot 164, and the RPM of the drive magnet 16 will correspond to the oscillary translation frequency of the tool 124. It will be appreciated by those skilled in the art that the distal most portion of the slot 164 should still place the tool magnet 122 within magnetic reach of the drive magnet 16. Otherwise, the tool magnet 122 could translate out of magnetic reach of the drive magnet 16. It is anticipated that the tool 124 utilized with this type of motion could be a file for filling down bone, though other types of tool known in the art could be utilized.

Figure 1D:
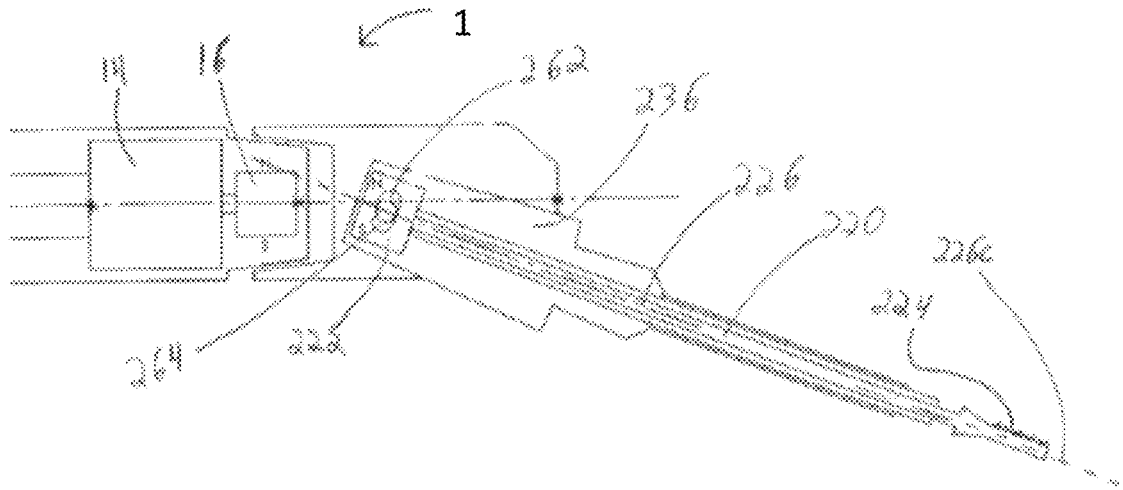
FIG. 1D is a schematic view of the medical tool system incorporating a third tool assembly included in a kit.

Turning to FIG. 1D, the instrument 10 is shown with another tool assembly 220 which allows for limited rotational movement (oscillation) about the shaft axis 226 $c$ but prevents longitudinal translation of the tool 224. The tool assembly 220 includes at least one attachment pin 262 extending from and fixed to at least one side of the tool magnet 222. The tool holder 236 defines a slot 264 which extends in a generally perpendicular direction relative to the shaft axis 226 $c$. This slot 264 thus prevents longitudinal translation of the tool magnet 222 and tool 224 along the shaft axis 226 $c$ (the pin 262 can only move along the slot 264 in the direction perpendicular to the shaft axis 226 $c$) while allowing for limited rotation (oscillation) of the tool magnet 222 and the tool 224 about the shaft axis 226 $c$.

Rotation of the drive magnet 16 by the motor 14 applies a force on the tool magnet 222 on account of the magnetic coupling therebetween. As the slot 262 limits movement of the tool 224 to rotational movement, the force will rotate the tool 224 in the direction induced by the drive magnet 16 until the pin 262 reaches the upper or lower limit of the slot 264, at which time the tool 224 will temporarily remain stationary until rotation of the tool magnet 222 (and thus the shaft 226 and tool 224) is induced in the other direction. Thus, one rotation of the drive magnet 16 will cause the tool 224 to move through the rotational range provided by the slot 264, and the RPM of the drive magnet 16 will correspond to the oscillary rotation frequency of the tool 224. It is anticipated that the tool 224 utilized with this type of motion could be a burr or cutter for removing material from the edges of a curved surface (e.g., sinus passages), though other types of tools known in the art could be utilized. The tool holder body 36 of the tool assembly 20 includes a proximal portion 36$a$, a distal end 36$b$, a narrow waist 36$c$ between the proximal portion 36$a$ and the distal end 36$b$, and a longitudinal bore 70 (FIG. 9) extending longitudinally through the entire tool holder body 36. The narrow waist 36$c$ facilitates manual gripping of the tool holder body 36 during removal and insertion of the tool assembly into the socket 34, and defines a slot 36$d$ (FIG. 4) (in communication with the longitudinal bore 70) to view indicia 88 (FIG. 2) provided on the cutting tool guard 80, which indicia indicate a relative positioning of the bur guard 80 relative to the tool holder body 36, and consequently a cutting depth of the bur 24. Alternatively, indicia 88 may be provided on the tool holder body 36 and a portion of the bur guard 80 can be referenced relative thereto. While the longitudinal slot 36$d$ shown in FIG. 4 extending through all of wall of the tool holder body 36 (e.g., from the bore 70 to the outer surface of the tool holder body 36), the longitudinal slot 36$d$ may extend only through a portion of the wall of the tool holder body 36.

Referring to FIG. 1A, the bearing sleeve 90 extends within the bore 70 and is longitudinally and preferably rotationally fixed relative to the bore 70, e.g., by interference engagement at a notch 96. The rotatable tool shaft 26 extends through the bearing sleeve 90. The tool shaft 26 is securely supported by but rotatable within the bearing sleeve 90 about a tool shaft axis 26$c$ coaxial with the bore axis 70$c$ of the bore 70, and is preferably made from flexible spring steel wire or tubing with an outer diameter in the range of 0.020 to 0.028 inches. The inner diameter of the sleeve 90 is preferably small enough to contact the tool shaft 26 to prevent wobbling or lateral movement of the tool shaft 26, but not so small as to restrict rotation or longitudinal translation of the tool shaft 26 relative to the bearing sleeve 90. The proximal end 26$a$ of the tool shaft 26 is coupled to a drive means for driving the shaft. In a preferred embodiment, the drive includes a drive magnet 22 (shown) for the magnetic drive system of the drill handpiece 10, or appropriate means for engagement with a pneumatic drive system, hydraulic drive system or a direct or reduction-gear electric drive system to provide for controlled high speed rotation of the tool shaft 26 and consequently the bur bit 24. Referring to FIG. 1A, the distal end 26$b$ of the tool shaft 26 carries a bur holder 98 that receives the bur bit 24. The bur holder 98 may be permanently integrated with the bur bit 24 or may be adapted to permit an exchange of one bit for another, i.e., selective release and secure capture of a bit. As shown in FIGS. 1A and 1B, the bur guard 80 has a notched distal end 80$b$ so that the bur bit 24 is partially guarded by the distal end 80$b$ of the guard. Specifically, the bur guard 80 defines a notch 80$c$ that extends proximally from the distal end 80$b$ of the guard 80 to a proximal end 80$d$ of the notch 80$c$. The notch 80$c$ leaves a portion of the side of the bur bit 24 unguarded, which provides visualization of a surgical field 81 to a user 83 while still presenting a flat edge 80$e$ of the bur guard 80 that acts as a stop for contact against bone or other tissue. Also, the notched end 80$b$ permits the user to rotate the bur 24 about the flat edge 80$e$ in the direction of the arrow A so that the cutting bit can cut deeper into the bone or tissue than the depth set by the bur guard 80. This may offer the user some flexibility to cut deeper than the depth set by the bur guard 80 without having to retract or stop the tool assembly 20 to adjust the cutting depth of the guard 80.

Preferably, the bur guard 80 is constructed of a plastically deformable metal such that the bur guard 80 and the bearing sleeve 90 may be manually bent along a curve by a surgeon or other user to retain such curved shape. If the guard 80 and sleeve 90 are bent by a user, then the portion of the shaft 26 inside of the guard 80 and sleeve 90 will simply bend with the guard 80 and sleeve 90. This allows the surgeon (i.e., a user) to facilitate an approach to the anatomy with the cutting bur 24 while holding the handpiece 10 at an angle offset from the rotational axis of the distal tip 24$b$ of the cutting bur 24, as may be advantageous for sight lines to the surgical field or for physical clearance relative to anatomical structure. It is nevertheless recommended, rather than significantly bending the guard 80 and sleeve 90, that a user utilize an appropriate angle mount or angle adjustable mount designed to orient the tool assembly 20 at the appropriate angle, as described in described in in previously incorporated U.S. Pat. No. 8,403,916. A user may then bend the guard and sleeve to make minor directional adjustments as needed.

Figure 2:
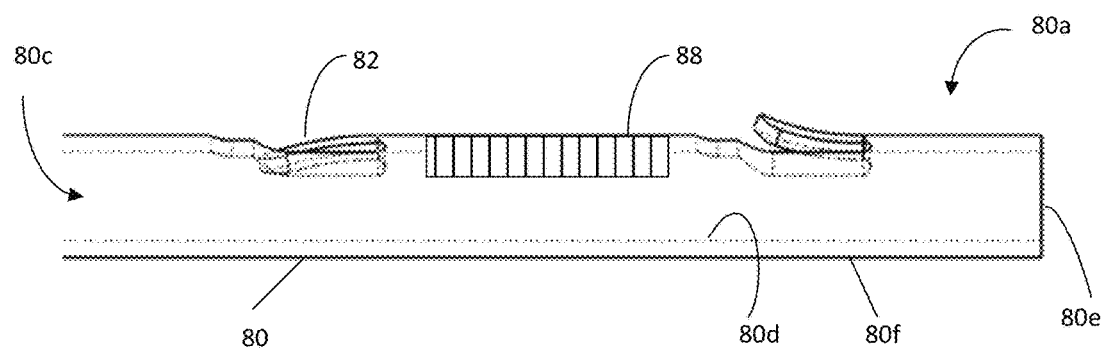
FIG. 2 shows a proximal end of a cutting tool guard of a cutting tool assembly of FIG. 1, shown in a first configuration.

The guard 80 is preferably a monolithic tube; i.e., a one-piece metal tubular construct having longitudinally spaced, radial cutouts defining a distal tab 82 and a proximal tab 84 both at the proximal end 80a of the guard 80, as shown in FIG. 2. The tabs 82 and 84 can be bent radially outward to engage the body 36 and/or radially inward to interact with an outer surface of the bearing sleeve 90, as will be described in greater detail below.

Figure 3:
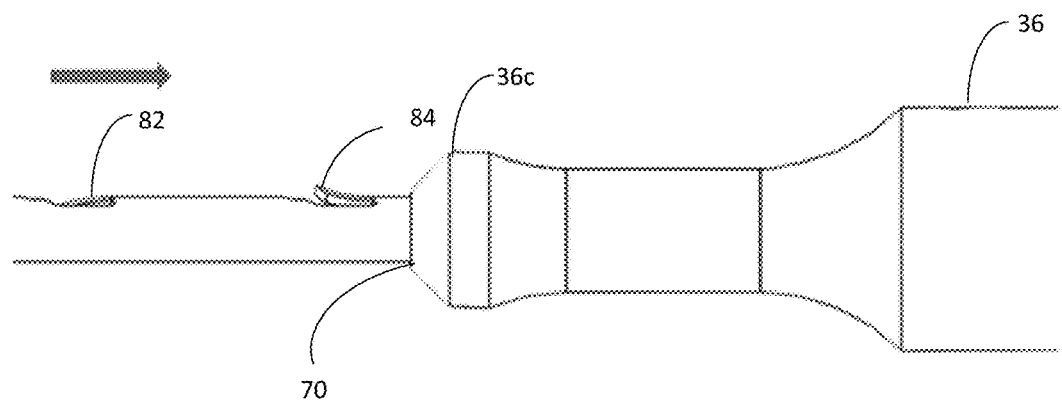
FIG. 3 shows the cutting tool guard of FIG. 2, partially inserted into a distal end of a tool holder body.

The proximal end 80a of the bur guard 80 is configured to be slid over the bur 26, bearing sleeve 90, and distal end 26b (FIG. 1A) of the shaft 26 towards the body 36 so that the proximal end 80a of the bur guard 80 is received in distal opening of the bore 70 in the body 36, as shown in FIG. 3. Before the bur guard 80 is slid over the bur 24, bearing sleeve 90, and distal end of the shaft 26, the bur guard 80 is configured into one of two configurations for either fixed or adjustable longitudinal movement with the tool holder body 36, as described in greater detail below.

FIG. 2 shows the proximal end of the bur guard 80 configured in a first configuration in which distal tab 82 is bent radially inwardly and proximal tab 84 is bent radially outwardly. In the first configuration, the bur guard 80 is configured for longitudinal adjustment relative to the bur 26 and the body 36, as will be described below. Thus, as will be described below, in the first configuration the bur guard 80 is adjustable between a fully retracted position shown in FIG. 5 and a fully extended position shown in FIG. 5A.

In FIG. 2 the proximal tab 84 is bent outwardly a sufficient distance from the outer surface of the bur guard 80 so that when the tab 84 is in the slot 36d (FIG. 4) of the body 36, it will cause an interference with the body 36 to retain the bur guard 80 relative to the body 36 and provide a positive stop to the extension of the bur guard 80 in the distal direction relative to the body 36. Also, the interference between the tab 84 and the slot 36d of the body 36 prevents relative rotation between the bur guard 80 and the body 36. The proximal tab 84 is bent radially outwardly from an outer surface 80f of the bur guard 80 such that it will not contact the outer surface of the bearing sleeve 90 when the bur guard 80 is slid over the bearing sleeve 90. The proximal tab 84 elastically deflects radially inwardly for insertion into the bore 70 at the distal end 36b of the body 36 and in to the slot 36d. The distal tab 82 is bent radially inwardly so that it protrudes into a hollow space 80c defined by an inner surface 80d of the bur guard 80, and far enough into the space 80c so that the tab 82 will frictionally engage (i.e., push against) an outer cylindrical surface of the bearing sleeve 90 when the bur guard 80 is slid over the bearing sleeve 90.

Figure 4:
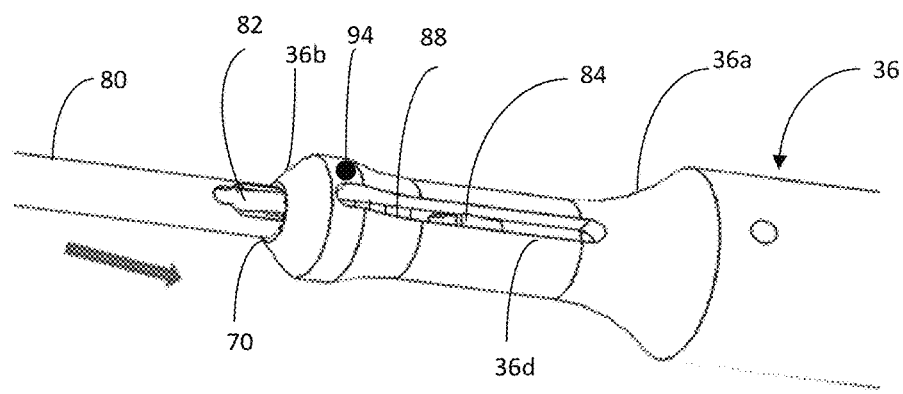
FIG. 4 shows the cutting tool guard shown in FIG. 3, inserted further in a proximal direction and engaged in a slot of the tool holder body.
Figure 5:
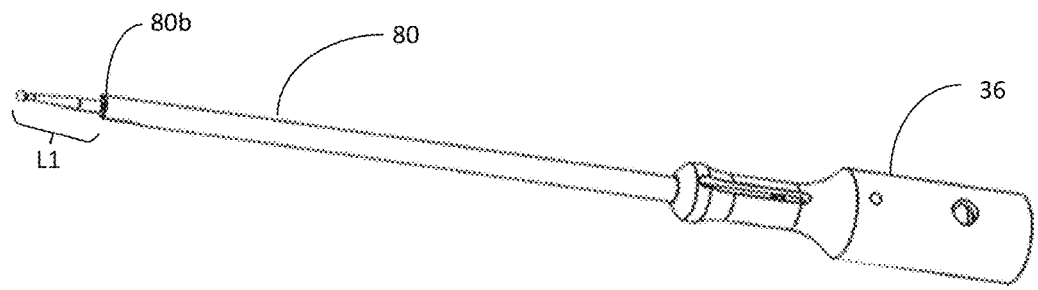
FIG. 5 shows the cutting tool guard in the first configuration shown in FIG. 4, inserted into a fully retracted position relative to the body of the tool assembly.

FIGS. 3 to 5 illustrate stages of connecting the bur guard 80 to the body 36 in which the bur guard 80 is shown configured in the first configuration. FIG. 3 illustrates inserting the proximal end 80a of the bur guard 80 through the bore 70 at the distal end 36b of the body 36 in the direction of the arrow. FIG. 4 illustrates a state where the guard 80 is pushed further into the bore 70 in the proximal direction of the arrow. When the guard 80 is pushed further into the bore 70 from the position shown in FIG. 2, the opening of the bore 70 at the distal end 36b of the body 36 will cause the proximal tab 84 to bend radially inwardly against the body 36 until the tab 84 clears the distal end of the slot 36d, whereupon the tab 84 resiliently deforms (snaps) back into its bent configuration shown in FIGS. 2 and 4. In FIG. 4, the proximal tab 84 is shows pushed towards the middle of the slot 36d, but can be displaceable throughout the slot 36d. From the position shown in FIG. 4, the bur guard 80 may be moved further in the proximal direction until a proximal end 80e (FIG. 2) contacts a proximal stop 70a (FIG. 9) within the bore 70 of the body 36, at which position the bur guard 80 may not be retracted any further proximally into the bore 70.

The position shown in FIG. 5 is, thus, a fully retracted position in which the extension of the bur 26 from the guard, and thus the cutting depth, is at a maximum. The bur guard 80 may be longitudinally translated between the fully retracted position shown in FIG. 5 to a fully extended position shown in FIG. 5A, and any position therebetween, by sliding the bur guard 80 in a distal direction relative to the body 36. As the bur guard 80 moves relative to the body 36, the distal tab 82 will continuously resiliently engage (e.g., compress against) the outer surface of the bearing sleeve 90 to cause a frictional engagement that will permit the guard 80 to be set in various positions without disturbing the position during use of the handpiece 20. As the bur guard 80 is displaced relative to the body 36, the exposed working length of the cutting bur extending from a distal end 80b of the guard 80 is altered (from $L_1$ to $L_2$), and a cutting depth of the bur 24 is thereby defined; i.e., the cutting bur 24 can cut no deeper than the length of which is exposed. Specifically, the distal end 80b of the bur guard 80 functions as a stop that will abut the bone, and that prevents cutting deeper than the defined cutting depth of the cutting bur 24. Thus, as described in more detail below, extension of the bur guard 80 allows the user to pre-set a penetration depth of the bur 24 into the cochlea and prevents penetration beyond to the delicate interior membranes.

Figure 5A:
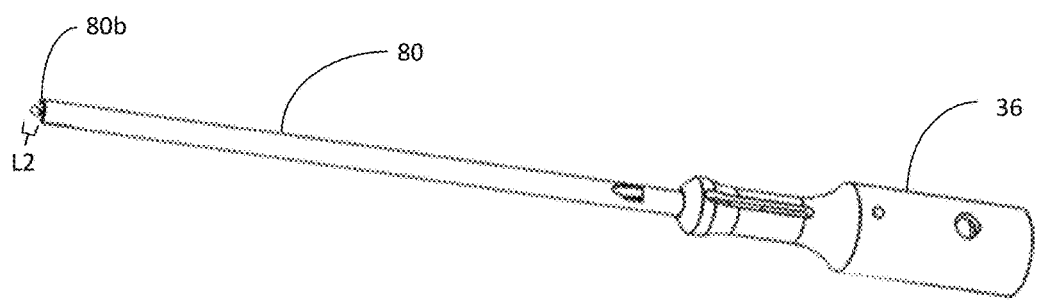
FIG. 5A shows the cutting tool guard in the first configuration displaced to a fully extended position.

Due to the interference between the proximal tab 84 and the body 36 at the distal end of the slot 36d, the bur guard 80 is limited in its distal travel beyond its fully extended position shown in FIG. 5A. Moreover, that interference locks the bur guard 80 to the body 36, such that the two cannot be readily separated from each other. It will be appreciated that the width of the slot 36d may be made sufficiently narrow to prevent user tampering with the tabs 82 and 84 inside the slot 36d. For example, in one embodiment, the slot 36d may have a width that is narrower than a user's finger so that the finger will not fit in the slot 36d to depress the tab 84 inwardly toward the bearing to clear the interference between the tab 84 and the bore 70. Such a tamper-proof arrangement effectively interlocks the bur guard 80 to the body 36. Regardless of the width of the slot 36d, an appropriately sized tool (not shown) can be used to depress tab 84 and release the guard 80 from the housing 36.

Figure 6:
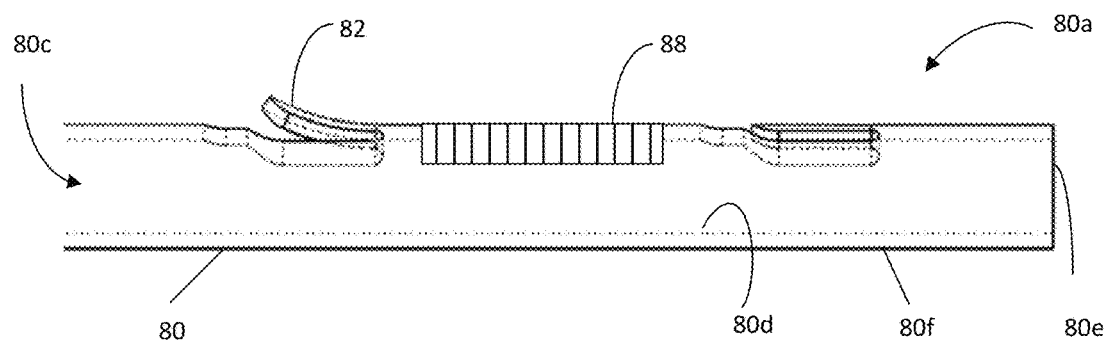
FIG. 6 shows a cutting tool guard of a cutting tool assembly of FIG. 1, shown in a second configuration.

Referring to FIGS. 2 and 4, the outer surface of the bur guard 80, between the distal tab 82 and the proximal tab 84, is formed with indicia 88 (by way of example graduated marks, letters: (A, B, C, D), numbers, other symbols, or a combination of two or more thereof) that when referenced relative to a registration mark 94 on the tool holder body 36 can be used to indicate the exposed length of the cutting bur 24 extending beyond the distal end 80b of the bur guard 80. The registration mark 94 may be located along the slot 36d, which may be used to define a viewing window through which to view the indicia 88 during adjustment of the bur guard 80. For example, a hash mark or dot may be provided on the outside surface of the body 36 near the distal end of the slot 36d so that alignment of indicia 88 with the mark 94 viewed through the slot 36d can be used to determine the cutting depth. Referring to FIGS. 4 and 6, in one embodiment, a plurality of the indicia 88 (e.g., letters A, B, C, D) may be provided to indicate, e.g., each 0.25 mm, or finer, of adjusted cutting depth, discussed further below. As discussed in detail below, the exposed length of the bur can preferably be set within a range of 0.1 mm to 5.0 mm with an accuracy of at least 0.5 mm, and more preferably 0.025 mm; although other suitable operable ranges and accuracies can be identified and set. It will also be appreciated that the positioning of the indicia may be reversed so that the indicia are provided along the slot 36d on the body 36 and the mark provided on the bur guard 80, such as between the tabs 82 and 84.

In use, the bur guard 80 is moved or otherwise set relative to the tool holder body 36 so that the distal end 80b of the bur guard 80 is even with the distal tip 24b of the cutting bur 24. The position of the indicia 88 relative to the registration mark 94 is noted by the user. Then, the bur guard 80 slid proximally to retract the distal end 80b of the bur guard 80 relative to the distal tip 24b of the cutting bur. Specifically, the indicia 88 provide relative depth indicator marks in relation to the registration mark 94. That is, once the initial position of the indicia 88 to the registration mark 94 is known, and it is known how far the bur guard 80 is retracted for the movement of each indicia past the registration mark, it can be determined the exact amount the bur guard 80 has been retracted for a given degree of translational movement of the bur guard 80 relative to the tool holder body 36.

The handpiece 10 may then be activated and used to cut hard tissues, particularly at the inner ear, including the hard outer tissue of the cochlea 100. The distal end of the tool assembly 20 is brought into contact with the cochlea, with the cutting bur 24 penetrating the hard outer tissue until the distal end of the bur guard contacts the tissue. At that time, the bur guard 80 functions as a stop to limit the depth of cutting, thereby protecting the delicate interior membranes of the cochlea. Moreover, even at the preset depth, the cutting bur may be used to cut laterally without interference from the bur guard, but with the bur guard maintaining its depth control function. The activation and use of the handpiece 20 may be the same as described in U.S. Pat. No. 9,155,545.

Figure 7:
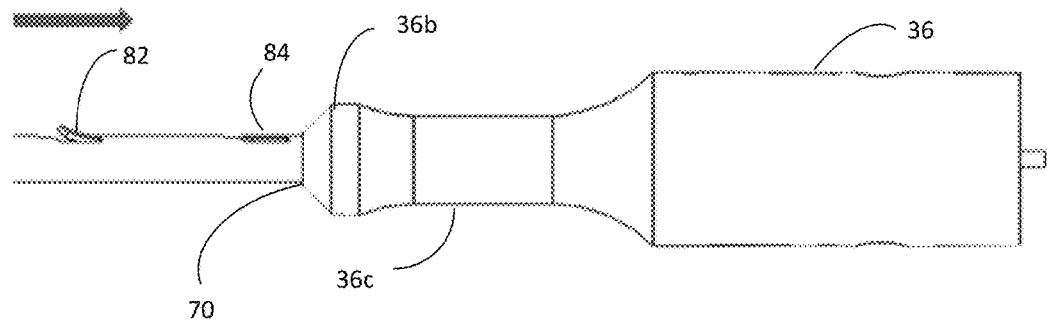
FIG. 7 shows the cutting tool guard of FIG. 6, partially inserted into a distal end of a body of a tool holder body.
Figure 10:
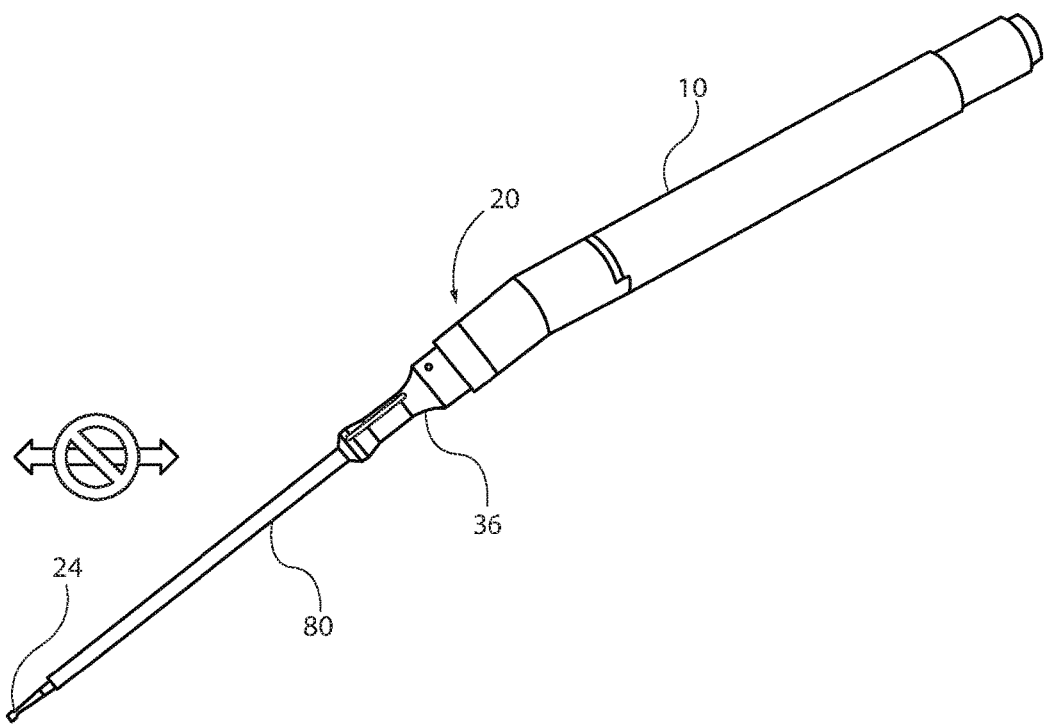
FIG. 10 shows the cutting tool system with the cutting tool guard in a fully retracted position.

FIG. 6 shows the bur guard 80 configured in a second configuration in which the bur guard 80 is non-adjustable and fixed in a fully retracted position when connected to the body 36, as shown in FIG. 10. As shown in FIG. 6, the distal tab 82 is bent radially outward from the interior space 80c of the guard 80, while the proximal tab 84 is left unbent. The bur guard 80, configured in the second configuration, may then be slid over the bur 24, bearing sleeve 90, and shaft 26 in the direction of the arrow in FIG. 7 through distal opening of bore 70 in the distal end 36b of the body 36.

Figure 8:
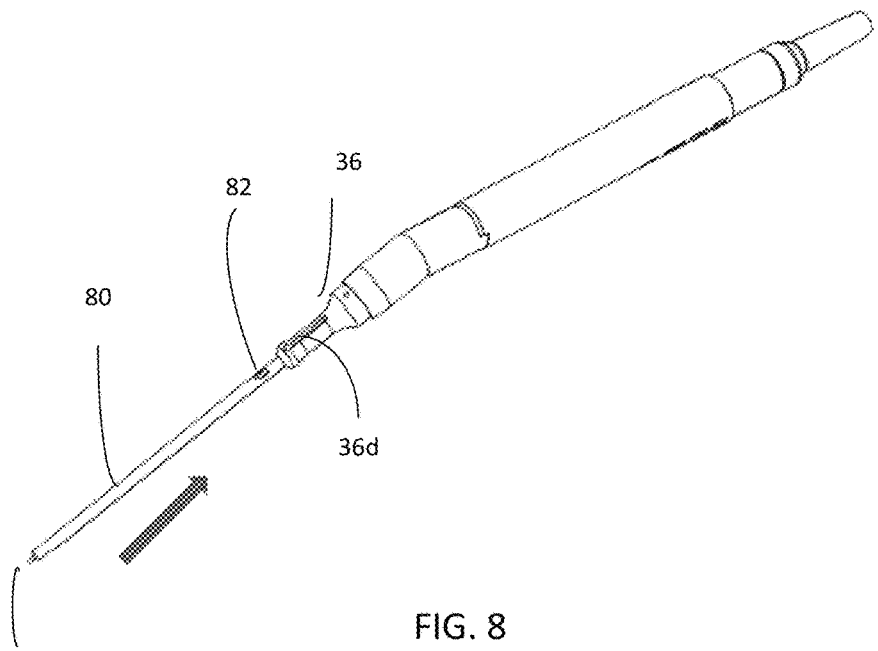
FIG. 8 shows the cutting tool guard shown in FIG. 7, inserted further in a proximal direction and engaged in a slot of the cutting tool holder body.
Figure 9:
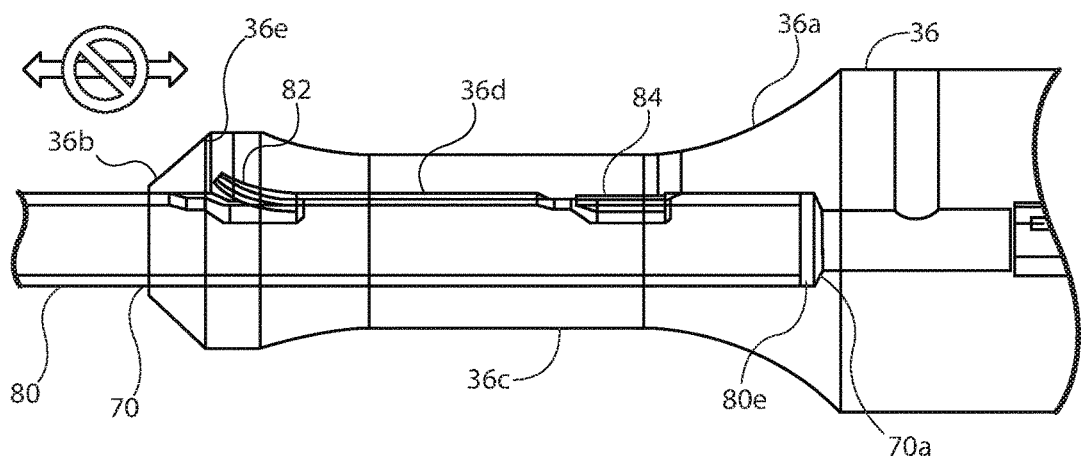
FIG. 9 shows the cutting tool guard in FIG. 8, inserted in a fully retracted position and locked in position in the slot of the cutting tool holder body.

When the bur guard 80 is slid further in the proximal direction, the proximal tab 84 passes through the bore 70 without engaging the body 36 and continues to be slid further in the direction of the arrow in FIG. 8 until the proximal end 80e (FIG. 6) of the bur guard 80 abuts stop 70a (FIG. 9) of the bore 70. When the proximal end 80e abuts stop 70a, the bur guard 80 cannot be slid any further in the proximal direction. Also, as shown in FIG. 9, when the bur guard 80 abuts the stop 70a, the deflected distal tab 82 abuts or is very closely spaced to a wall 36e of the slot 36d at the distal end of the slot 36d, such that the guard 80 cannot readily slide distally relative to the body 36 out of the bore 70. Thus, in the position shown in FIGS. 9 and 10, the guard 80 is effectively locked in a single, fully retracted position. The guard 80 may be unlocked or otherwise released from the body 36 by depressing tab 82 while pulling the guard 80 and body 36 apart longitudinally.

In use, the proximal end 80a of the bur guard 80, in its second configuration, is slid into locking engagement with the body 36, as described above. Once the bur guard 80 is locked to the body 36, the handpiece 20 is then activated and used to cut hard tissues, particularly at the inner ear, including the hard outer tissue of the cochlea 100. The distal end of the tool assembly is brought into contact with the cochlea, with the cutting bur 24 penetrating the hard outer tissue until the distal end of the bur guard contacts the tissue. At that time, the bur guard 80 functions as a stop to limit the depth of cutting, thereby protecting the delicate interior membranes of the cochlea. Moreover, even at the preset depth, the cutting bur may be used to cut laterally without interference from the bur guard, but with the bur guard maintaining its depth control function. The activation and use of the handpiece 20 may be the same as described in U.S. Pat. No. 9,155,545.

FIGS. 11A to 13 illustrate a system 301, similar to system 1, in which like reference numbers represent the same elements. The system 301 includes a handpiece 310, a tool mount 318, and a tool assembly 320. The handpiece 310 includes a housing 312, an electric motor (not shown) mounted within the housing, a drive magnet (not shown) coupled to and rotated by the motor, and a tool mount 318 preferably detachably coupled to the housing 312, but optionally fixed relative thereto.

As shown in FIGS. 11B to 12B, the tool mount 318 defines a socket 334 for receiving a tool holder body 336 of the tool assembly 320 in an interference fit. As shown in greater detail in FIG. 12B, a projection 322 extends radially inward from an inner wall 334a of the socket 334 to a free end 322a. A marking 322b (FIGS. 11B, 11C, and 12A) may be displayed on the outside 334b of the socket 334 at a location that is opposite the free end 322a. The marking 322b can provide a visual indication, externally of the system 301, of the position of the projection 322 on the inside of the socket 334. As described in greater detail below, the projection 322 is configured to align with a slot 338 of the tool assembly 320 body 336.

Figure 11A:
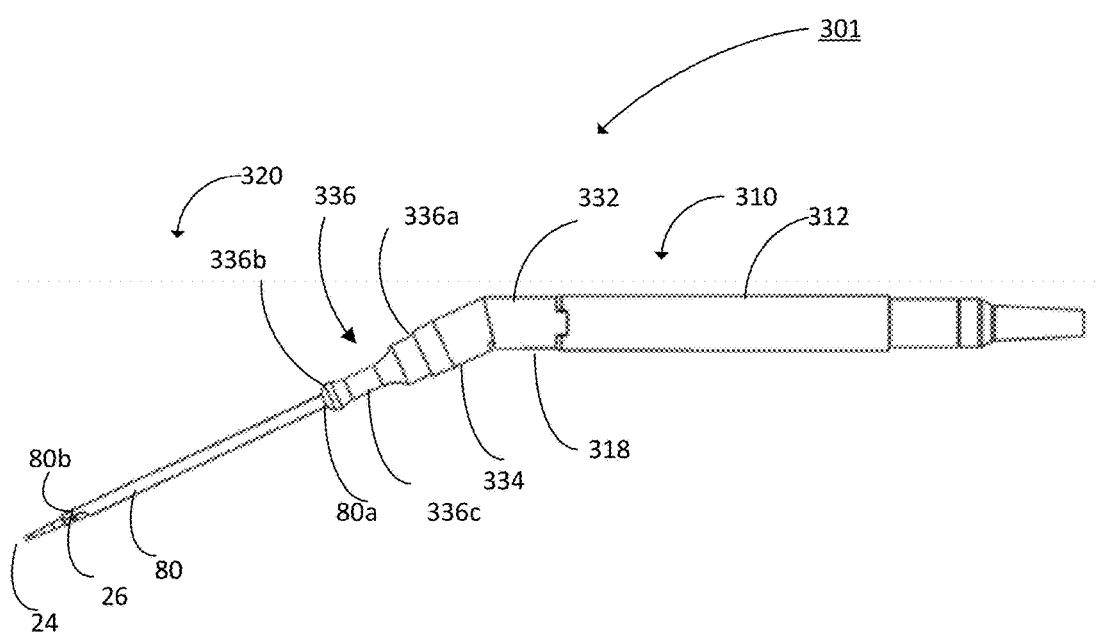
FIG. 11A shows another embodiment of a cutting tool system in accordance with an aspect of the invention.
Figure 11B:
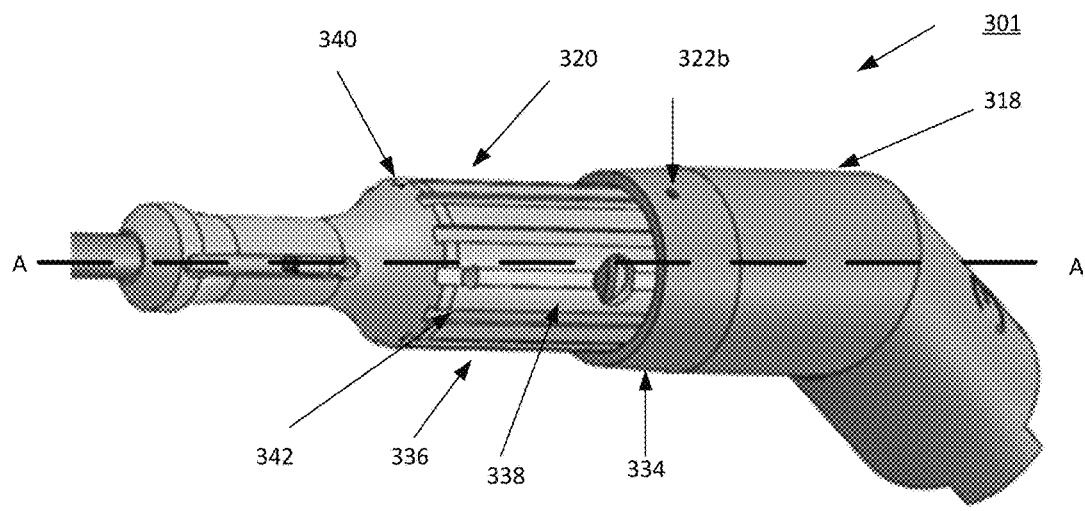
FIG. 11B shows a detailed view of a portion of the system of FIG. 11A in a first configuration.
Figure 11C:
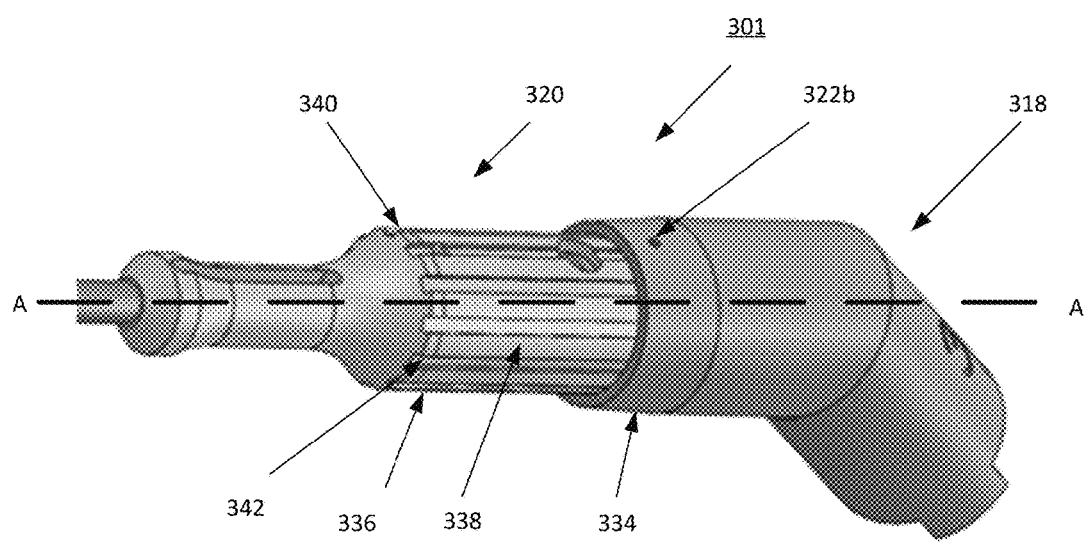
FIG. 11C shows a detailed view of a portion of the system of FIG. 11A in a second configuration.
Figure 12A:
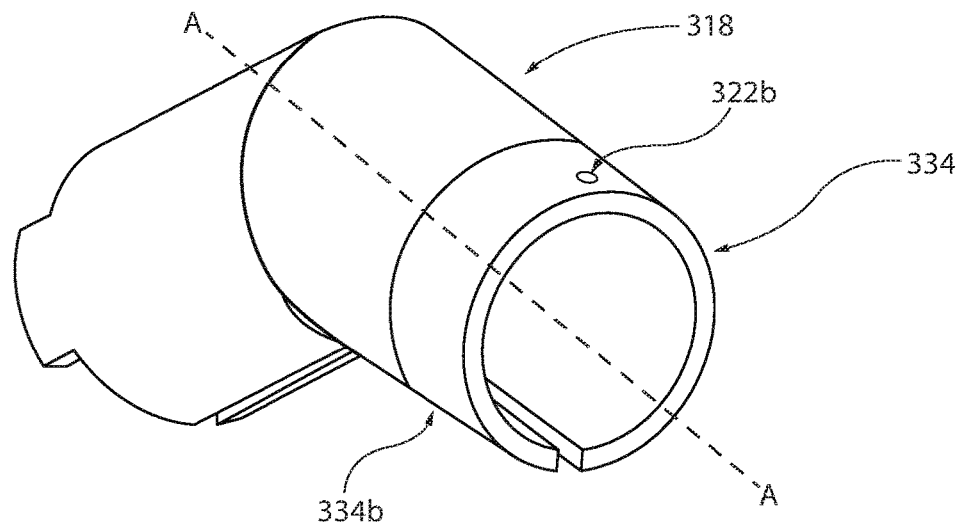
FIG. 12A is an isometric view of a tool mount of the system shown in FIG. 11A, viewed from a top and side of the tool mount.
Figure 12B:
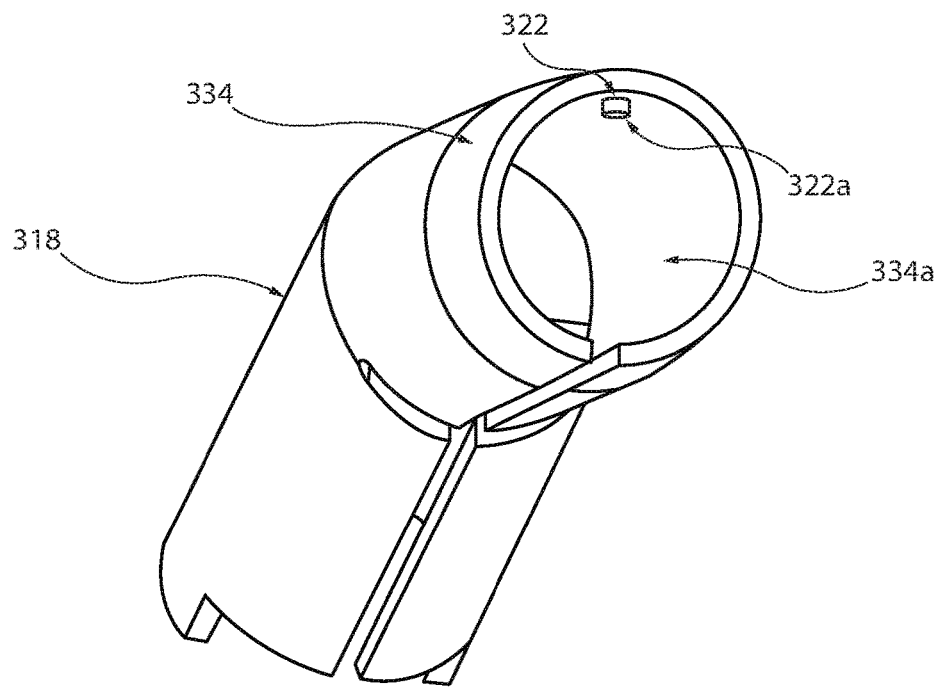
FIG. 12B is an isometric view of the tool mount of the system shown in FIG. 11A, viewed from a bottom and side of the tool mount.
Figure 13:
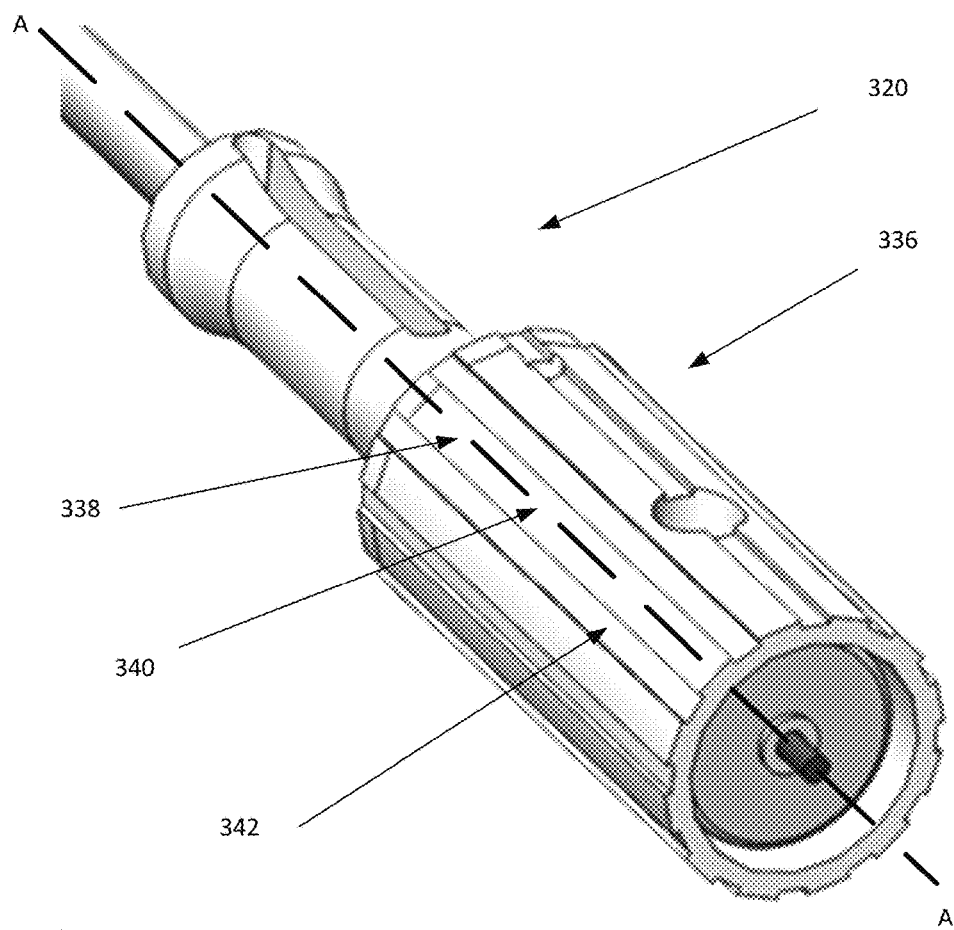
FIG. 13 is an isometric view of a body of a tool assembly of the system shown in FIG. 11A.

As shown in FIGS. 11B, 11C, and 13, the tool holder body 336 of the tool assembly 320 has a tapered outer surface 340, which defines at least one ridge 342 and groove or slot 338. The ridge 342 and slot 338 extend longitudinally along the surface 340 generally parallel to axis A-A. In the embodiment shown in FIGS. 11B, 11C, and 13, a plurality of longitudinal slots 338 are circumferentially spaced from each other an equal amount by the ridges 342.

The tool assembly 320 may be coupled to the handpiece 310 in the same manner as tool assembly 20 and handpiece 10, i.e., by a tapered interference fit between a proximal end of the body 336 of the tool assembly 320 and the socket 334 of the handpiece 310. In addition to the interference fit, as noted above, the slots 338 are configured to align with and receive the projection 322 when the tool assembly 320 is inserted into the socket 334. The projection 322 has a radial length that extends up to the depth of the slots 338, so as not to affect the interference fit between the tool assembly 320 and the handpiece 310. Also, preferably, a width of the projection 322 is slightly less than the circumferential width of the slots 338 to limit relative rotation between the tool assembly 320 and the handpiece 310 when they are coupled together. Limiting the relative rotation between the tool assembly 320 and the handpiece 310 may be useful if friction is not sufficient to maintain the interference fit between the tool mount 318 of the handpiece 310 and the tool assembly 320. For example, if a sufficiently large bur is used in the tool assembly 20, described above, it may be possible to generate a large enough torque in the tool assembly that may otherwise generate relative rotation between the tool assembly 20 and the handpiece 10 if not constrained.

Also, owing to the plurality of slots 338, the projection 322 may be aligned with and received in any one of the slots 338, such that a user can orient the notched distal end 80b of the bur guard 80 with respect to the handpiece 310 for greater visibility to the user. For example, FIG. 11B shows a first relative angular positioning between the handpiece 310 and the tool assembly 320, and FIG. 11C shows a second relative angular positioning between the handpiece 310 and the tool assembly 320. Of course, where the number of slots 338 increases, the user has finer control of adjusting the relative angular positioning of the tool assembly 320 with respect to the handpiece 310 about axis A-A.

While the projection 322 has been described as extending from the socket 334 and configured to be received in slots 338 in the body 336, in at least one alternative embodiment (not shown), the positioning of the projection and the slots may be reversed, such that the projection may extend from the body 336 of the tool assembly and slots 338 are defined on the inner surface 334a of the socket 334 to receive the projection.

There have been described and illustrated herein embodiment of a system, tool assembly, and a method of using the system and tool assembly that restricts tool depth. While particular embodiments of the invention have been described, it is not intended that the invention be limited thereto, as it is intended that the invention be as broad in scope as the art will allow and that the specification be read likewise. Thus, while a particular snap fit sliding mating between the guard and the tool holder body has been disclosed, it will be appreciated that another relative coupling can be used as well, provided that such mating allows for either continuous or discrete longitudinal displacement of the guard relative to the holder body to allow setting of a working length of the cutting tool. Also, while a bur has been shown as an exemplar medical tool, other tools can similarly be provided to the distal end of the shaft, including a cutter, a drill, a file, a saw, or any number of other similar devices. Also, while the medical tool and shield have been described with respect to performing a surgical procedure on the inner ear (at the cochlea), it is appreciated that the medical tool and shield may be used in other otological procedures, and even other procedures on various parts of the human anatomy located near to or away from otological structure. By way of example only, the medical tool and shield can be sized to perform arthroscopic procedures in the body. It will therefore be appreciated by those skilled in the art that yet other modifications could be made to the provided invention without deviating from its spirit and scope as claimed.

What is claimed is:

1. A tool assembly for use with a surgical tool handpiece coupled to a tool mount having a socket for receiving the tool assembly, comprising:
   a) a tool holder body having a proximal portion with a proximal end, a distal portion with a distal end, and defining a longitudinal bore extending between the proximal and distal ends and defining a longitudinal slot extending through all or a portion of a wall of the tool holder body and in communication with the longitudinal bore, the proximal portion adapted for engagement with the socket of the tool mount, and the bore defining a bore axis;
   b) a tool shaft having a proximal end and a distal end, the tool shaft extending within the bore and permanently retained relative to the tool holder body, and the tool shaft movable relative to a tool shaft axis, the proximal end of the tool shaft having a structure configured to be moved by the surgical tool handpiece;
   c) a medical tool coupled relative to the distal end of the tool shaft, such that relative movement of the tool shaft results in a corresponding movement of the tool, the tool having a length;
   d) a bearing sleeve retained in the bore and extending around the tool shaft, the shaft extending within and freely movable relative to the bearing sleeve; and
   e) a tool guard having a proximal end, a distal end and a central portion, the bearing sleeve disposed in an annular space between the tool guard and the tool shaft, the tool guard being a tubular member having a plurality of longitudinally spaced tabs formed in a wall of the tube, the tabs being radially deformable into a plurality of configurations with the bearing sleeve and for retentive engagement with the tool holder body, and the distal end of the tool guard having an opening sized to permit advancement of the tool therethrough, the tool freely movable relative to the tool guard, wherein relative longitudinal translation of the tool guard relative to the holder body longitudinally displaces the distal end of the tool guard relative to the holder body and sets a defined working length of the length of the tool extending beyond the distal end of the tool guard,
   wherein the working length is adapted to be constant while the tool shaft is retained in the socket of the tool mount and wherein the handpiece drives movement of the tool shaft.

2. The tool assembly according to claim 1, wherein:
the tool shaft is configured for at least one of 360 degree rotation about the tool shaft axis, oscillatory rotation about the tool shaft axis, and longitudinal translation along the axis.

3. The tool assembly according to claim 2, wherein:
the medical tool is a cutter, a drill, or a file.

4. The tool assembly according to claim 1, wherein:
the longitudinal translation is without rotation.

5. The tool assembly according to claim 4, wherein:
the plurality of longitudinally spaced tabs comprises has a proximal tab and a distal tab at the proximal end of the tool guard, wherein the proximal tab and the distal tab are longitudinally aligned and spaced from one another.

6. The tool assembly according to claim 5, wherein:
at least one of the proximal tab and the distal tab are radially bendable to configure the tool guard in one of a first configuration in which the working length is fixed and a second configuration in which the working length is adjustable.

7. The tool assembly according to claim 6, wherein:
the tool guard is configured in the first configuration when the distal tab is bent radially outward and wherein the tool guard is configured in the second configuration when the distal tab is bent radially inward and the proximal tab is bent radially outward.

8. The tool assembly according to claim 7, wherein in the second configuration, the distal tab is configured to frictionally engage the bearing sleeve to limit longitudinal movement between the tool guard and the tool.

9. The tool assembly according to claim 7, wherein in the first configuration, the distal tab is configured to snap fit through the bore of the tool holder body by sliding the tool guard proximally into the bore.

10. The tool assembly according to claim 7, wherein in the second configuration, the proximal tab is configured to snap fit through the bore of the tool holder body by sliding the tool guard proximally into the bore.

11. The tool assembly according to claim 10, wherein when the proximal tab is snap fit, the distal end of the tool guard is positionable between a retracted position and an extended position relative to the tool by longitudinally translating the tool guard within the tool holder body.

12. The tool assembly according to claim 1, wherein:
at least one tab of the plurality of longitudinally spaced tabs is configured for frictional engagement with the bearing sleeve.

13. The tool assembly according to claim 1, wherein:
one of the tool holder body and the tool guard includes a registration mark and the other of the tool holder body and the tool guard includes indicia, and referencing the indicia relative to the registration mark provides an indication of the working length of the tool.

14. The tool assembly according to claim 13, wherein:
the tool guard includes the indicia between the tabs and the tool holder body is provided with the registration mark, and wherein the indicia on the tool guard are viewable through a window defined by the slot in the tool holder body.

15. The tool assembly according to claim 1, wherein:
the tool guard has a notched distal end that exposes a portion of the tool.

16. A surgical tool system, comprising:
a) a surgical tool handpiece, including,
a housing,
a tool mount detachably coupled to the housing and having a socket, and
drive means for driving a replaceable tool assembly coupled to the socket of the tool mount; and
b) the replaceable tool assembly detachably coupled within the socket, the tool assembly including,
i) a tool holder body having a proximal portion with a proximal end, a distal portion with a distal end, and defining a longitudinal bore extending between the proximal and distal ends and defining a longitudinal slot extending through all or a portion of a wall of the tool holder body and in communication with the longitudinal bore, the proximal portion adapted for engagement with the socket of the tool mount, and the bore defining a bore axis;
ii) a tool shaft having a proximal end and a distal end, the tool shaft extending within the bore and permanently retained relative to the tool holder body, and the tool shaft movable about a tool shaft axis, the proximal end of the tool shaft being driveable by the drive means;
iii) a medical tool coupled relative to the distal end of the tool shaft, such that movement of the tool shaft results in corresponding movement of the tool, the tool having a length;
iv) a bearing sleeve retained in the bore and extending around the tool shaft, the shaft extending within and freely rotatable relative to the bearing sleeve; and
v) a tool guard having a proximal end, a distal end and a central portion, the bearing sleeve disposed in an annular space between the tool guard and the tool shaft, the tool guard being a tubular member having a plurality of longitudinally spaced tabs formed in a wall of the tube, the tabs being radially deformable into a plurality of configurations with the bearing sleeve and for retentive engagement with the tool holder body, and the distal end of the tool guard having an opening sized to permit advancement of the tool therethrough, the tool freely movable relative to the tool guard, wherein relative longitudinal translation of the tool guard relative to the holder body longitudinally displaces the distal end of the tool guard relative to the holder body and sets a defined working length of the length of the tool extending beyond the distal end of the tool guard, wherein the working length is adapted to be constant while the handpiece drives the tool shaft.

17. The tool system according to claim 16, wherein:
the tool shaft is configured for at least one of 360 degree rotation about the tool shaft axis, oscillatory rotation about the tool shaft axis, and longitudinal translation along the axis.

18. The tool system according to claim 17, wherein:
the medical tool is a cutter, a drill, or a file.

19. The tool system according to claim 16, wherein:
the longitudinal translation is without rotation.

20. The tool system according to claim 16, wherein:
at least one tab of the plurality of longitudinally spaced tabs is configured for frictional engagement with the bearing sleeve.

21. The tool system according to claim 16, wherein:
the tool guard has a notched distal end that exposes a portion of the tool.

22. A method of drilling with a surgical handpiece, comprising:
a) providing a surgical tool system including,
i) a surgical tool handpiece, and
ii) at least one replaceable tool assembly detachably coupled relative to a socket of the handpiece, the tool assembly including,
A) a tool holder body having a proximal portion with a proximal end, a distal portion with a distal end, and defining a longitudinal bore extending between the proximal and distal ends and defining a longitudinal slot extending through all or a portion of a wall of the tool holder body and in communication with the longitudinal bore, the proximal portion adapted for engagement with the socket of the handpiece, and the bore defining a bore axis;
B) a tool shaft having a proximal end and a distal end, the tool shaft extending within the bore and permanently retained relative to the tool holder body, and the tool shaft movable relative to a tool shaft axis, the proximal end of the tool shaft having a structure by which the surgical tool handpiece is adapted to drive movement of the tool shaft about the tool shaft axis;
C) a medical tool coupled relative to the distal end of the tool shaft, such that movement of the tool shaft results in corresponding movement of the tool, the tool having a length;
D) a bearing sleeve retained in the bore and extending around the tool shaft, the shaft extending within and freely movable relative to the bearing sleeve; and
E) a tool guard having a proximal end, a distal end and a central portion, the bearing sleeve disposed in an annular space between the tool guard and the tool shaft, the tool guard being a tubular member having a plurality of longitudinally spaced tabs formed in a wall of the tube, the tabs being radially deformable into a plurality of configurations with the bearing sleeve and for retentive engagement with the tool holder body, and the distal end of the tool guard having an opening sized to permit advancement of the tool therethrough, the tool freely movable relative to the tool guard, wherein relative longitudinal translation of the tool guard relative to the holder body longitudinally displaces the distal end of the tool guard relative to the holder body and sets a defined working length of the length of the tool extending beyond the distal end of the tool guard, wherein the working length is adapted to be constant while the handpiece applies torque to the tool shaft;

b) longitudinally displacing, without rotation of the tool guard, the tool guard relative to the holder body by a set distance to define an exposed working length of the tool between the distal end of the tool guard and a distal tip of the tool; and c) applying the tool to tissue within the exposed working length of the tool.

23. The method according to claim 22, wherein:
the tool guard and the tool holder body are coupled relative to each other by a mating, and wherein the displacing is carried out by translation of the tool guard relative to the tool holder body.

24. The method according to claim 22, wherein:
one of the tool holder body and the tool guard includes a registration mark and the other of the tool holder body and the tool guard includes indicia, and referencing the indicia relative to the registration mark provides an indication of the exposed working length of the tool.

25. The method according to claim 22, wherein:
the tissue is inner ear tissue.

26. The method according to claim 25, wherein:
the inner ear tissue is a cochlea.

27. The method according to claim 22, wherein:
at least one of the tabs of the plurality of longitudinally spaced tabs is bent radially outward relative to the wall of the tube prior to the displacing.

28. The method according to claim 27, wherein:
at least one of the tabs of the plurality of longitudinally spaced tabs is bent radially inward relative to the wall of the tube prior to the displacing.

29. The method according to claim 27, further comprising:
releasing the tool guard from the tool holder body by depressing the radially outward bent tab and pulling the tool guard away from the body.

30. The method according to claim 22, further comprising:
applying until the tissue contacts the distal end of the tool guard.

* * * * *